(12) United States Patent
Hulliger

(10) Patent No.: US 9,055,987 B2
(45) Date of Patent: Jun. 16, 2015

(54) KIT FOR IMPLANTING HEAT DEFORMABLE FIXATION ELEMENTS OF DIFFERENT SIZES

(75) Inventor: Urs Hulliger, Langendorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 537 days.

(21) Appl. No.: 13/283,095

(22) Filed: Oct. 27, 2011

(65) Prior Publication Data

US 2012/0157977 A1 Jun. 21, 2012

Related U.S. Application Data

(60) Provisional application No. 61/424,949, filed on Dec. 20, 2010.

(51) Int. Cl.
*A61B 18/20* (2006.01)
*A61B 18/22* (2006.01)
*A61B 17/88* (2006.01)

(52) U.S. Cl.
CPC ............ *A61B 17/8863* (2013.01); *A61B 18/20* (2013.01); *A61B 18/22* (2013.01); *A61B 17/8872* (2013.01)

(58) Field of Classification Search
None
See application file for complete search history.

(56) References Cited

U.S. PATENT DOCUMENTS

| | | | | |
|---|---|---|---|---|
| 4,666,405 A * | 5/1987 | Ericson | ........................ | 433/229 |
| 4,911,712 A * | 3/1990 | Harrington | .................... | 606/14 |
| 5,462,544 A * | 10/1995 | Saksena et al. | ................. | 606/15 |
| 5,593,425 A * | 1/1997 | Bonutti et al. | ................. | 606/232 |
| 5,634,711 A * | 6/1997 | Kennedy et al. | .............. | 362/119 |
| 5,662,712 A * | 9/1997 | Pathak et al. | ............. | 623/23.64 |
| 5,711,665 A * | 1/1998 | Adam et al. | ....................... | 433/9 |
| 5,779,706 A | 7/1998 | Tschakaloff | | |
| 6,033,223 A * | 3/2000 | Narusawa et al. | ............ | 433/226 |
| 6,102,696 A * | 8/2000 | Osterwalder et al. | ........... | 433/29 |
| 6,193,510 B1 * | 2/2001 | Tsimerman | .................... | 433/29 |
| 6,200,134 B1 * | 3/2001 | Kovac et al. | ..................... | 433/29 |
| 6,331,111 B1 * | 12/2001 | Cao | ................................. | 433/29 |
| 6,419,483 B1 * | 7/2002 | Adam et al. | .................... | 433/29 |
| 6,602,074 B1 * | 8/2003 | Suh et al. | ................... | 433/228.1 |
| 7,024,717 B2 * | 4/2006 | Hilscher et al. | ................ | 15/22.1 |
| 7,119,515 B2 * | 10/2006 | Senn et al. | ..................... | 320/106 |
| 7,182,597 B2 * | 2/2007 | Gill et al. | ........................ | 433/29 |
| 7,194,180 B2 * | 3/2007 | Becker | ........................ | 385/134 |
| 7,335,205 B2 * | 2/2008 | Aeschlimann et al. | ........ | 606/232 |
| 8,249,696 B2 * | 8/2012 | Fisher et al. | ................. | 600/476 |

(Continued)

FOREIGN PATENT DOCUMENTS

| | | |
|---|---|---|
| EP | 2221014 | 8/2010 |
| WO | 2008/095327 | 8/2008 |
| WO | WO 2009036576 A1 * | 3/2009 |

*Primary Examiner* — Lynsey Crandall
*Assistant Examiner* — Manolis Pahakis
(74) *Attorney, Agent, or Firm* — Baker & Hostetler LLP

(57) ABSTRACT

A device for implanting heat deformable fixation elements of different sizes in a bone, comprises a hand piece extending from a proximal end to a distal end and including an internal optical waveguide connected to a laser source and open to the distal end of the hand piece and a light guiding tip extending from a proximal end to a distal end, the proximal end of the light guiding tip being removably mechanically and optically connectable to the distal end of the hand piece and the distal end of the light guiding tip being configured to permit removable attachment of a bone fixation element, the light guiding tip including an optical waveguide, wherein the light guiding tip is configured to control a total radiant energy Q transmitted from the laser source to the bone fixation element.

14 Claims, 5 Drawing Sheets

(56) References Cited

U.S. PATENT DOCUMENTS

| | | |
|---|---|---|
| 2002/0177099 A1* | 11/2002 | Cao .................................. 433/29 |
| 2005/0282102 A1* | 12/2005 | Kert .................................. 433/29 |
| 2007/0011836 A1* | 1/2007 | Brewer et al. ................. 15/220.1 |
| 2007/0270221 A1* | 11/2007 | Park et al. ....................... 463/37 |
| 2007/0270833 A1* | 11/2007 | Bonutti et al. .................. 606/61 |
| 2008/0209650 A1* | 9/2008 | Brewer et al. ................... 15/22.1 |
| 2009/0112196 A1* | 4/2009 | Rabiner et al. .................. 606/13 |
| 2009/0323733 A1* | 12/2009 | Charkas ............................ 372/5 |
| 2010/0121419 A1* | 5/2010 | Douglas ........................... 607/90 |
| 2010/0241229 A1* | 9/2010 | Baehre et al. ............... 623/16.11 |
| 2011/0245819 A1* | 10/2011 | Nardini et al. .................. 606/13 |
| 2012/0129131 A1* | 5/2012 | Baehre et al. .................. 433/173 |
| 2013/0052607 A1* | 2/2013 | Gersh et al. ..................... 433/27 |

\* cited by examiner

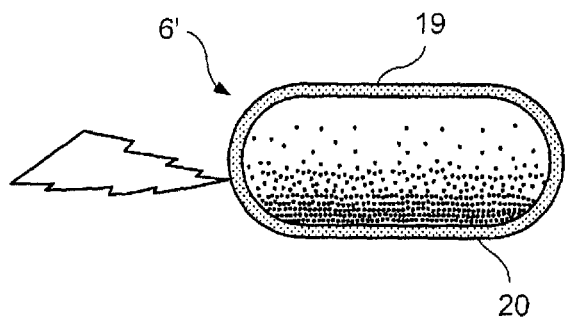
FIG. 12
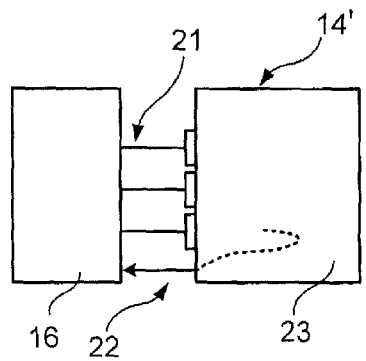
FIG. 13
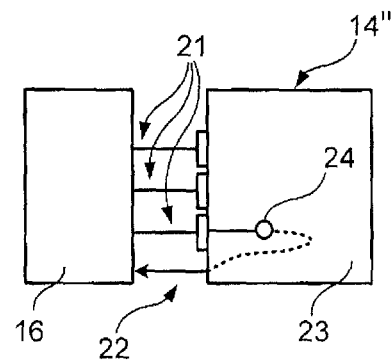
FIG. 14
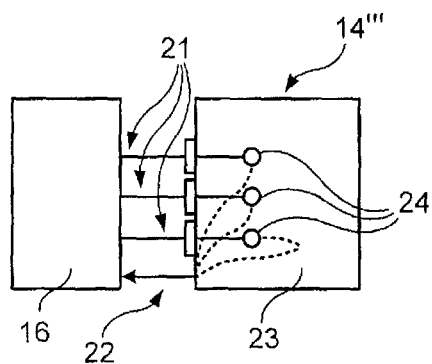
FIG. 15
| Code 0 | 0 | 0 | 0 |
| Code 1 | 1 | 0 | 0 |
| Code 2 | 0 | 1 | 0 |
| Code 3 | 0 | 0 | 1 |
| Code 4 | 1 | 1 | 0 |
| Code 5 | 0 | 1 | 1 |
| Code 6 | 1 | 0 | 1 |
| Code 7 | 1 | 1 | 1 |
FIG. 16

KIT FOR IMPLANTING HEAT DEFORMABLE FIXATION ELEMENTS OF DIFFERENT SIZES

PRIORITY CLAIM

The present application claims priority to U.S. Provisional Application Ser. No. 61/424,949 entitled "Kit for Implanting Heat Deformable Fixation Elements of Different Sizes" filed on Dec. 20, 2010, the entire disclosure of which is incorporated herein by reference thereto.

FIELD OF THE INVENTION

The present invention generally relates to a kit for implanting fixation elements of different sizes in a bone. More particularly, the present invention relates to a kit for implanting heat deformable fixation elements of different sizes.

BACKGROUND OF THE INVENTION

Fixation elements (e.g., pegs, screws, pins) are well known in the field of bone fixation and consist completely or partly of thermoplastic materials which can be softened or melted completely or preferably at their surface by application of electromagnetic radiation (e.g. laser light) thereto. Softening or melting of the thermoplastic material permits the fixation elements to adapt their shape to a surrounding cavity (e.g. a plate hole or a bore in a bone) to achieve a better anchorage therewithin. In some cases, the softened or melted thermoplastic material can penetrate into cavities and slits of surrounding bone material so that a particularly efficient anchorage takes place.

However, present fixation elements prevent a determination of an optimal amount of energy needed to properly anchor the fixation element in the bone, instead relying only on rough estimates based on various parameters (e.g., thermoplastic material, volume of the fixation element, absorptive properties of the thermoplastic material or possibly contained chromophores therein, and power of the light source). The subjective estimation can lead to an irradiation duration that is either too short or too long, thus reducing an efficacy of a fixation element anchoring procedure. Specifically, if the irradiation period is too short, the fixation element undergoes an insufficient softening and is unable to adapt to a shape of a bone or other environment in which it is implanted, thus causing a poor anchorage. If the irradiation period is too long, an excessive liquefaction of the fixation element results, permanently damaging the mechanical stability of the fixation element. Furthermore, depending upon the supplied excessive quantity of energy, over-irradiation can also lead to an overheating of the thermoplastic material to further reduce an anchoring strength of the fixation element in the bone.

BRIEF SUMMARY OF THE INVENTION

The invention relates to a kit for the implantation of bone fixation elements that are deformable by means of energy input, the bone fixation elements being configured to allow an optimal fixation within a bone.

The present invention relates to a kit for implanting heat deformable fixation elements of different sizes, comprising a hand piece having a laser source able to emit a radiant flux $\Phi$ and an internal optical waveguide connected to the laser source and leading to a distal end of the hand piece. The kit also comprises $N \geq 2$ light guiding tips extending between proximal end distal ends and having an optical waveguide, the proximal end being mechanically and optically connectable to the distal end of the hand piece and the distal end of the tip having a removable fixation element attached thereto. The kit further comprises a means for automatically controlling the total radiant energy Q transmitted from the laser source to the fixation element depending on the type of light guiding tip connected to the hand piece.

The kit of the invention provides the advantage of higher security and reduced possibilities of error due to an automatic selection of the optimal energy duration relative to the size of the fixation element. The kit of the invention also offers convenient operation with a smaller risk of contamination when changing a tip thereof. That is, since the entire disposable tip is changed between procedures, the possibility of cross-contamination via, for example, a contaminated optical fiber, is substantially reduced and/or eliminated.

The volume of the fixation element according to the invention (e.g., a bone fixation pin) is preferably in a range of about 4 mm$^3$ to about 400 mm$^3$ and the surface of the fixation element is preferably in a rage of 2 mm$^2$ to 240 mm$^2$. The optical waveguides of the light guiding tip are connected to the optical waveguides of the hand piece and configured to operate at full power, the total energy transmitted to the fixation element being controlled by the optical waveguides of the exemplary kit of the invention. A laser source connected to the hand piece can be provided with an internal power supply (e.g., a battery or an accumulator) or can comprise a connecting cable to an external electric network. A further advantage of the kit according to the invention is that the interface can be remote from the surgical intervention site.

In a special embodiment of the kit, the hand piece comprises a timer with a fixed time period $t_F$. The laser source is able to emit a constant radiant flux $\Phi_1$ and at least one of the light guiding tips comprises a laser light absorbing means reducing the radiant flux $\Phi_1$ received from the hand piece to a radiant flux $\Phi_2 < \Phi_1$ transmitted to the fixation element. In this embodiment, a total radiant energy $Q = \Phi_2 t_F$ is emitted from the laser source through the internal optical waveguide of the hand piece and through the optical waveguide of the light guiding tips to the fixation element. The means for automatically controlling the total radiant energy Q comprises the timer and, if present, the laser light absorbing means. If a light guiding tip of the kit does not comprise a laser light absorbing means, a total radiant energy $Q = \Phi_1 t_F$ is transmitted to the fixation element attached to the light guiding tip.

In a further embodiment of the kit, the ratio $\Phi_2$ to $\Phi_1$ is in the range of 1 to 15.

In a further embodiment of the kit, the hand piece comprises a timer, the laser source has a constant radiant flux $\Phi_1$, and at least one light guiding tip comprises a set-point means which, upon connection of the light guiding tip to the hand piece, controls the timer to activate the laser source for a time period $t_V$ so that a total radiant energy $Q = \Phi_1 t_V$ is emitted from the laser source through the internal optical waveguide of the hand piece and through the optical waveguide of the light guiding tips to the fixation element.

In another embodiment of the kit, the time period $t_V$ is chosen in relation to a size of the fixation element. This embodiment permits the application of an appropriate amount of energy to each of the fixations elements attached to the different light guiding tips.

In another embodiment of the kit, the time period $t_V$ is chosen in relation to the surface area of the fixation element.

In again another embodiment of the kit, the time period $t_V$ of the timer is selected in a range of 2 to 12 seconds. When performing a bone fixation procedure in a hand of a patient, the time $t_V$ may be in the range of 4 to 8 seconds. When performing bone fixation procedures in the lower extremities of a patient, the time $t_F$ may be in the range of 2 to 6 seconds.

In a further embodiment of the kit, the hand piece comprises a timer for the laser source with a constant time period $t_F$, the laser source has a selectively variable radiant flux $\Phi_V$, and at least one of the light guiding tips comprises a set-point means which, upon connection of the guiding tip to the hand piece, induces a microprocessor to control the magnitude of radiant flux $\Phi_V$. The timer has a fixed time period $t_F$ to activate the laser source so that a total radiant energy $Q=\Phi_y \cdot t_F$ is emitted from the laser source through the internal optical waveguide of the hand piece and through the optical waveguide of the light guiding tip to the fixation element.

In a further embodiment of the kit, the constant time $t_F$ of the timer is chosen in the range of 2 to 15 seconds, preferably in the range of 2 to 10 seconds. Typically, the constant time $t_F$ is 5 seconds. When performing a bone fixation procedure in a hand of a patient, the constant time $t_F$ is in the range of 4 to 8 seconds. When performing bone fixation procedures in the lower extremities, the constant time $t_F$ is in the range of 2 to 6 seconds.

In still a further embodiment of the kit, the radiant flux $\Phi_V$ is chosen in relation to the volume of the fixation element.

In another embodiment of the kit, the radiant flux $\Phi_V$ is chosen in relation to the surface area of the fixation element.

In another embodiment of the kit, the variable radiant flux $\Phi_V$ is chosen in a range of 2 W to 32 W.

In again another embodiment of the kit, the total radiant energy $Q=\Phi t$ is in the range of 2 to 32 Ws.

In yet another embodiment of the kit, two or more light guiding tips comprise fixation elements of different sizes and respectively different set-point means that define the time period $t_F$ for the timer or induce the microprocessor to control the magnitude of radiant flux $\Phi_V$ of the laser source. This embodiment has the advantage that the different fixation elements attached to the light guiding tips are heated up by transmission of an individually defined total radiant energy.

In a further embodiment of the kit, the set-point means are electrically connectable to the microprocessor via a number M of electrical contacts, the set-point means transferring a code determining the time period $t_F$ or the magnitude of radiant flux $\Phi_V$ to the microprocessor.

In a further embodiment of the kit, the code is defined by a number P≤M of activated electrical contacts in the set-point means and/or by the position of the activated electrical contacts at the set-point means. Alternatively, the code can be defined by the number Q of electrical contacts attached to the set-point means and/or by the position of the number Q of electrical contacts attached to the set-point means.

In another embodiment of the kit, one end of the hand piece is mechanically and optically connectable to the first end of the light guiding tip so that the laser light is transmittable from the laser source to the fixation element by the internal optical waveguide and the optical waveguides.

In another embodiment of the kit, the laser light is transmitted through the internal optical waveguide and through the optical waveguide of the light guiding tip.

In again another embodiment of the kit, the fixation element comprises a thermoplastic material, preferably chosen from the group consisting of: polyacetylenes, polyanilines, poly(ethylenedioxythiophenes), poly(phenylenevinylines), polyarylenes, polyspiro-bifluorenes, polydialkylfluorenes, polythiophenes and polypyrroles.

In yet another embodiment of the kit, the fixation element comprises a polymer or several polymers compatible with the body. The polymer material may comprise a colored substance, have a reflecting coating, be capable of receiving colored substances in contact with body fluids containing colored substances or be self-colored. The colored polymer, colored-substance containing polymers, or any polymer layers that border the reflecting coatings, color-receiving coatings or coatings containing a color layer are all capable of being heated and softened via electromagnetic radiation.

In still another embodiment of the kit, only a predetermined portion of the polymer material is colored.

In a further embodiment of the kit, the constant radiant flux $\Phi_1$ emitted by the laser source is in the range of 0.5-20 W.

The term optical waveguide, as used in the description, refers to a flexible or rigid optical light-transmitting structure, such as for instance a glass fiber cable or reflecting hose (e.g. a nanotube) used to transmit electromagnetic radiation from the source to the fastener.

The term photoconductivity/light transmittance, as used in the description, refers to optically transparent implants capable of transmitting electromagnetic radiation (e.g., glass). This photoconductivity may also be specific for the radiation introduced, or other wavelengths may be reflected or absorbed. It may however be desirable, in certain embodiments of the invention, that certain areas in or on the implant be able to diffuse light so as to achieve a uniform distribution thereof. This diffusing effect may be achieved by using crystals, bubbles, fractures, phase boundaries of any kind, foreign bodies or pigments of any kind, admixtures of polymers, and/or ceramic substances (e.g., particulates of calcium phosphate).

The term laser types, as used in the description, refers to lasers that typically emit only a few narrowly defined frequencies of electromagnetic radiation. The absorption spectra of one or more chromophores of the non-absorbing portion of the fixation element as well as of surrounding tissue may thus be selected to be attuned to one other. In a preferred application, the laser radiates in a preferably monochromatic frequency that is barely absorbed by the implant, strongly by the chromophore, and again only barely by the surroundings. This makes it possible to supply different areas with different chromophores in the implant, and to specifically warm them up with the electromagnetic radiation frequency that may be preferred on a case-by-case basis.

One or more of the radiation frequencies that are especially well absorbed by the chromophore pigment in the polymer or by the light-absorbing polymer are particularly preferred.

All currently used laser types, swinging modes, pulsating or continuous wave operations should be included. The preferred types are diode lasers of the infrared or visible spectrum. Under certain conditions it is also desirable to employ polarized radiation, for instance by employing polarization filters in the implant or on the radiating source, or for instance electromagnetic radiation already generated in a polarized form. The polarization can thus be utilized as a means for selecting the targeted warming-up of the implant, especially when employing chromophores that are preferably excitable by polarized light.

The preferred wavelength of electromagnetic radiation lies in the range between 260 and 3,000 nm, preferably in the visible range and in the near infrared range of up to 1,200 nm. However, other wavelengths are also conceivable. The shape of the light radiation may be of any kind, such as with a cross section of an oval, rectangular, star-shaped, triangular, bundled-ray form, etc.

The tables below indicate a non-exhaustive list of employable lasers in connection with the kit of the invention:

|  | Wavelength(s) |
| --- | --- |
| Gas laser | |
| Helium-neon laser | 632.8 nm (543.5 nm, 593.9 nm, 611.8 nm, 1.1523 μm, 1.52 μm, 3.3913 μm |
| Argon laser | 454.6 nm, 488.0 nm, 514.5 nm (351 nm, 457.9 nm, 465.8 nm, 476.5 nm, 472.7 nm, 528.7 nm) |
| Krypton laser | 416 nm, 530.9 nm, 568.2 nm, 647.1 nm, 676.4 nm, 752.5 nm, 799.3 nm |
| Xenon ion laser | Various wavelengths from UV to infrared |
| Nitrogen laser | 337.1 nm |
| Carbon dioxide laser | 10.6 μm (9.4 μm) |
| Carbon monoxide laser | 2.6 to 4 μm, 4.8 to 8.3 μm |
| Exciter laser | 193 nm (ArF), 248 nm (KrF), 308 nm (XeCl), 353 nm (XeF) |
| Chemical lasers | |
| Hydrogen fluoride laser | 2.7 to 2.9 μm, |
| Deuterium fluoride laser | ≈3800 nm (3.6 to 4.2 μm) |
| COIL (Chemical oxygen-iodine laser) | 1.315 μm |
| Color laser | |
| Color laser | 390-435 nm (stilbene), 460-515 nm (coumarin 102), 570-640 nm (rhodamine 6G), and others |
| Metal-vapor laser | |
| Helium-cadmium (HeCd) metal-vapor laser | 441.563 nm, 325 nm |
| Helium-mercury (HeHg) metal-vapor laser | 567 nm, 615 nm |
| Helium-selenium (HeSe) metal-vapor laser | up to 24 wavelengths between red and UV |
| Copper-vapor laser | 510.6 nm, 578.2 nm |
| Gold-vapor laser | 627 nm |
| Solid material laser | |
| Ruby laser | 694.3 nm |
| Nd:YAG laser | 1.064 μm, (1.32 μm) |
| Er:YAG laser | 2.94 μm |
| Neodymium YLF (Nd:YLF) solid material laser | 1.047 and 1.053 μm |
| Neodymium-doped yttrium orthovanadate (Nd:YVO$_4$) laser | 1.064 μm |
| Neodymium-doped yttrium calcium oxoborate laser, Nd:YCa$_4$O(BO$_3$)$_3$ or simply Nd:YCOB | ≈1.060 μm (≈530 nm at the second harmonic) |
| Neodymium glass (Nd:glass) laser | ≈1.062 μm (silicate glasses), ≈1.054 μm (phosphate glasses) |
| Titanium sapphire (Ti:sapphire) laser | 650-1100 nm |
| Thulium YAG (Tm:YAG) laser | 2.0 μm |
| Ytterbium YAG (Yb:YAG) laser | 1.03 μm |
| Ytterbium doped glass laser (rod, plate/chip, and fiber) | 1 μm |
| Holmium YAG (Ho:YAG) laser | 2.1 μm |
| Cerium-doped lithium strontium (or calcium) aluminum fluoride (Ce:LiSAF, Ce:LiCAF) | ≈280 to 316 nm |
| Promethium 147 doped phosphate glass ($^{147}$Pm$^{+3}$:Glass) solid-state laser | 933 nm, 1098 nm |
| Chromium doped chrysoberyl (alexandrite) laser | Typically 700 to 820 nm |
| Erbium doped and erbium-ytterbium codoped glass lasers | 1.53-1.56 μm |
| Trivalent uranium doped calcium fluoride (U:CaF$_2$) solid state laser | 2.5 μm |
| Divalent samarium doped calcium fluoride (Sm:CaF$_2$) laser | 708.5 nm |
| F-center laser | 2.3-3.3 μm |
| Semiconductor laser | |
| Semiconductor laser diode | 0.4-20 μm, depending on the material |
| GaN | 0.4 μm |
| AlGaAs | 0.63-0.9 μm |
| InGaAsP | 1.0-2.1 μm |
| Lead salt | 3-20 μm |
| Vertical cavity surface emitting laser (VCSEL) | 850-1500 nm, depending on the material |
| Quantum cascade laser | Infrared |
| DPSS-laser | UV-infrared |
| Hybrid silicon laser | Infrared |

After heating, the fixation element (e.g., a pin) may be inserted under pressure in a cavity (e.g., a bone cavity) and adapted to conform to the geometry of the cavity. The fixation element may then also be inserted under pressure into interspaces surrounding the fixation element within the bone so that after the fixation element has cooled and solidified, a secure anchoring is achieved by geometric coupling with the bone.

The term chromophore, as used in the description, refers to coloring substances or pigments added to the polymer to absorb electromagnetic radiation and convert the radiation to heat.

A special application according to the invention also allows employing substances that are added to the a coating or a core material of the implant, the substances lacking chromophore properties. These substances are configured to change properties upon contact with body tissue, preferably as a reaction to the pH of the tissue, to body salts, body moisture or body temperature. The change in properties discolors the substance and renders it capable of absorbing electromagnetic radiation. Accordingly, this embodiment permits only the portion of the implant contacting body tissue to be heated.

In general, the following chromophores and pigments should be explicitly included: chlorophyll, carbon black, graphite, fluorescein, methylene blue, indocyanine green, eosine; eosine Y (514 nm), ethyleosine (532 nm), acridine, acridine orange, copper phtalocyanine, chrome-cobalt-aluminum oxide, ferrous ammonium citrate, pyrogallol, logwood extract, chlorophyll-copper complex, D&C blue No. 9, D&C green No. 5, [phtalocyaninate(2-)] copper, D&C blue no. 2, D&C blue no. 6, D&C green no. 6, D&C violet no. 2, and D&C yellow No. 10. In certain instances, fluorescent chromophores or polymers that under certain circumstances do not absorb but rather radiate light that is absorbed from their surroundings, may also be employed.

Fusing, softening or plasticizing of the fixation element material according to the invention is intended to refer to a softening of the fixation element which occurs in response to heat generated by the absorption of radiation.

The term light-absorbing, non-colored polymer, as used in the description, refers to polymers having a properties configured to absorb light of a certain wavelength without the need of adding a chromophore thereto. In one particular embodiment according to the invention, the light-absorbing polymer is preheated to the point of discoloring spontaneously and thus becoming capable of absorbing more light. In an extreme case, the light-absorbing polymer is partially carbonized or caramelized to become light-absorbent.

In a further embodiment according to the invention, the implant consists at least partially of a polymer to be heated, the polymer exhibiting a minimum molar heat capacity cp of 1.6 kJ/kmolK, and preferably of 2.2 kJ/kmolK.

In a further embodiment according to the invention, the implant consists at least partially of a polymer to be heated, the polymer exhibiting a minimum molar heat capacity cp of 2.9 kJ/kmolK, and preferably of 2.5 kJ/kmolK. The molar heat capacity may range from 1.9 to 2.7 kJ/kmolK.

In a further embodiment according to the invention, the polymer is selected so that softening occurs below a warming temperature of 250° C.

In a further embodiment according to the invention, softening of the polymer occurs below a softening temperature of 150° C., preferably under 100° C.

In one more embodiment according to the invention, the polymer to be heated and softened is a thermoplastic material.

In one more embodiment according to the invention, the thermoplastic material is chosen from the following groups: poly-alpha-hydroxyester, polyorthoester, polyanhydride, polyphosphazines, poly(propylenefumarate), polyesteramide, polyethylenefumarate, polylactide, polyglycolide, polycaprolacton, trimethylenecarbonate, polydioxanone, polyhydroxybutyrate, as well their copolymers and mixtures thereof.

Apart from the polymer containing a color material or being self-coloring, the fixation element may also comprise additional materials, preferably chosen from the group consisting of: metals, carbon, ceramics, PEEK, non thermoplastic polymers that are preferably chosen from the group consisting of polymethylmethacrylate and/or inorganic materials such as potassium phosphate, calcium sulphate or bone cement.

In order to achieve a local heating of the fixation element, substances or optical elements may be introduced into the implant which, while not significantly absorbing electromagnetic radiation, possess the property of shifting the frequency of light, such as typically frequency doubling crystals or frequency multiplying crystals. In this case, long-wave light passes through the fixation element without causing a heating thereof until a portion of the fixation element having the frequency-altering (e.g., doubling) characteristic is reached. The long-wave light then warms this portion of the fixation element and exits this portion of the fixation element with a shorter frequency, while being absorbed to a significantly greater degree by the remainder of the fixation element. This effect can also be repeated several times. Typical substances employed to achieve this effect may include non-linear optical substances, for instance lithium niobate ($LiNbO_3$), potassium dihydrogen phosphate (KDP), beta-bariumborate ($\beta$-$BaB_2O_4$ or BBO), lithium triborate or DAST (diethylamino-sulfurtrifluoride). In a similar manner, even phase transitions or boundary layers having the same effect can be integrated in or on the fixation element.

In one example according to the invention, an absorbable osteosynthesis plate of 1 mm thickness made of a poly-D, L-lactide may be applied to bone fragments to be fixated, and the necessary holes may be drilled into the bone. In one embodiment, the plate may be fitted with holes for 2 mm screws. Holes of 1.7 mm size are drilled into the bone. A partially light-conducting pin, which is attached at the front of the light guiding tip of 2.0 mm diameter, is then passed through the screw hole in the plate, arranged on the pre-drilled hole and impacted with light (at a power of 3 Watt and wavelength of 808 nm). The energy of the light flowing through the light conducting pin causes a heating thereof. By subsequently applying a soft pressure on the pin, the pin may be pushed into the predrilled hole in the bone, and the thermoplastic material could be made to flow into the accessible inter-trabecular interspaces in the cancellous bone. The instrument with the light source is then retracted. The polymer material cools and solidifies in less than approximately one minute.

In another embodiment according to the invention, the exemplary system and method disclosed above may be applied for the insertion and fixation of an intramedullary nail into the bone wherein the softenable pin of the kit is inserted into the pre-drilled holes in the bone and into locking holes extending through the intramedullary nail.

In yet another embodiment according to the invention, a thread may be affixed to a tendon or another portion of a bone the pin having a transverse hole extending therethrough to receive a suture material having a high melting point. A hole with a diameter of 3 mm.-15 mm. may be drilled into the bone. The pin with the thread attached may then be inserted into the bone hole, the pin being subsequently heated. Once cooled, the pin and thread are effectively anchored in the bone.

BRIEF DESCRIPTION OF THE DRAWINGS

Several embodiments of the invention will be described in the following by way of example and with reference to the accompanying schematic drawings in which:

FIG. 12 illustrates a schematic view of an energy absorbing glass capsule as a variant to the laser light absorbing means of the first embodiment of the kit according to the invention;

FIG. 13 illustrates the microprocessor and different setpoint means according to a first mode of operation according the invention;

FIG. 14 illustrates the microprocessor and different setpoint means according to a second mode of operation according the invention;

FIG. 15 illustrates the microprocessor and different setpoint means according to a third mode of operation according the invention; and FIG. 16 shows a table defining different codes of the setpoint means according to the invention.

DETAILED DESCRIPTION OF THE INVENTION

The present invention is directed to a system and method for the fixation of a bone by implanting a device into the bone, a portion of the device including a material configured to be softened upon application of heat to aid in anchoring the device to the bone. In particular, the present invention is directed to a device comprising one or more bone fixation elements formed of, for example, a biocompatible polymer having material properties (e.g., color, reflective coating, etc.) configured to aid in fixation thereof in a target location of the bone. The exemplary system and method according to the invention also comprises a handpiece configured to guide insertion of the fixation element to a target portion of the bone. The exemplary handpiece is configured to transport laser light from a laser light source provided therein to one or more light guiding tips operably connected thereto. The light guiding tips further guide the laser light to the fixation elements. As will be described in greater detail below, a number of light guiding tips used in a particular application may have a direct correlation to a size of the fixation element, with a greater number of light guiding tips being used for larger fixation elements, as would be understood by those skilled in the art. It is noted, however, that any number of light guiding tips may be used in any application without deviating from the spirit and scope of the invention. Upon application of laser light, the fixation element is heated and softened to conform to a required dimension and/or to bond to one or more biological or implanted structures to ensure proper bone fixation. In one example, the bonding may be performed by melting the biological or implanted structures to one another. The exemplary light source according to the invention is further connected to a timer to control a flow of laser light thereof, as will be described in greater detail later on. That is, once the fixation element is heated, it may conform to a shape of the target region of the bone, including any cracks and crevices, to provide a sufficient holding strength with the bone. It is noted that the term "proximal" as used herein refers to a direction approaching a physician or other user of the device while the term "distal" refers to a direction approaching a target treatment area in a patient.

Figure 1:
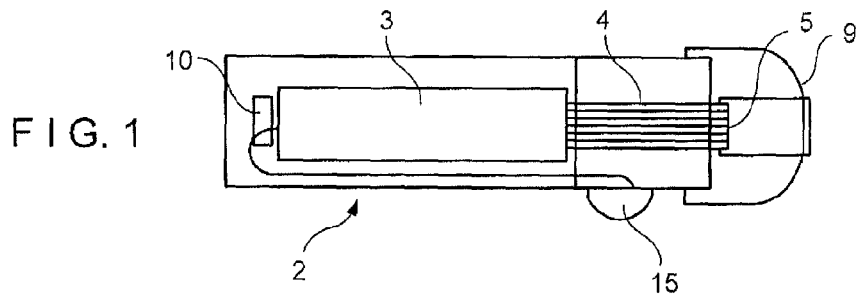
FIG. 1 illustrates a longitudinal section through the hand piece of a first kit according to the invention.
Figure 2A:
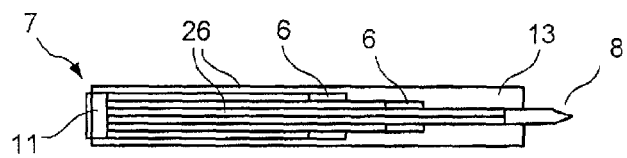
FIG. 2a illustrates a longitudinal section through a first light guiding tip for the first kit according to the invention.
Figure 2B:
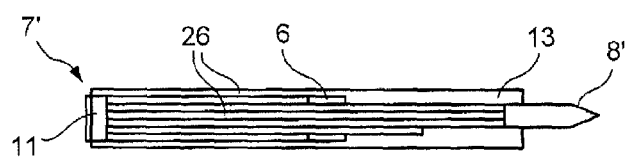
FIG. 2b illustrates a longitudinal section through a second light guiding tip for the first kit according to the invention.
Figure 2C:
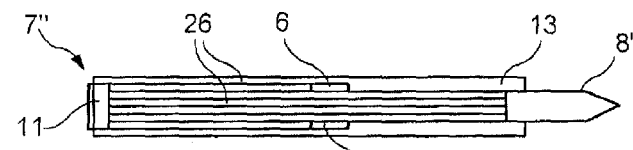
FIG. 2c illustrates a longitudinal section through a third light guiding tip for the first kit according to the invention.
Figure 2D:
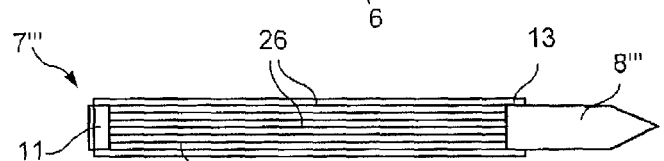
FIG. 2d illustrates a longitudinal section through a fourth light guiding tip for the first kit according to the invention.
Figure 3:
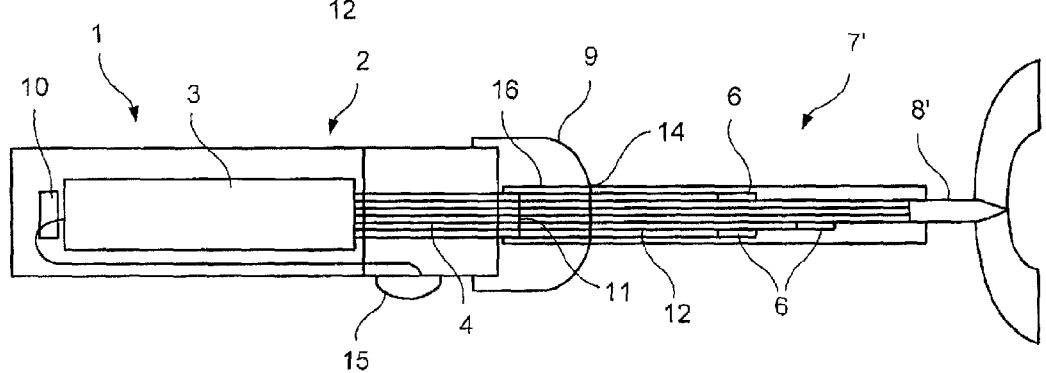
FIG. 3 illustrates a longitudinal section through the hand piece and a light guiding tip attached thereto of the first embodiment of the kit according to the invention.

FIGS. 1-3 depict a kit 1 according to a first exemplary embodiment of the invention, the kit 1 comprising a hand piece 2. The hand piece 2 comprises a laser source 3 optically and mechanically connected to an internal optical waveguide 4. The waveguide 4 is configured to transport laser light emitted by the laser source 3 to a light guiding tip 7 and further includes a timer 10 and a cap 9 coupling the hand piece 2 to the light guiding tip 7. The laser source 3 is configured to emit a constant radiant flux $\Phi_1$. The internal optical waveguide 4 extends from the laser source 3 to a distal end 5 of the hand piece 2. The distal end 5 of the hand piece 2 may be connectable to a proximal end 11 of the light guiding tip 7 by a bayonet or a click connection to optically and coaxially connect the internal optical waveguide 4 to the optical waveguide 12. The hand piece 2 further comprises a trigger button 15 that actuates the timer 10 to activate the laser source 3. The timer 10 is configured with a fixed time period $t_F$ so that the laser source 3 is automatically switched off after expiration of the allowed fixed time period $t_F$. The cap 9 has a central cavity 16 extending from a distal surface 14 to the distal end 5 of the hand piece 2 so that the proximal end 11 of the light guiding tip 7 can be inserted therethrough.

FIGS. 2a-2d illustrate a selection of different light guiding tips 7 according to the invention, wherein like elements are referenced with like reference numerals. Each light guiding tip 7, 7', 7'', 7''' extends from the proximal end 11 to a distal end 13. A fixation element 8 (e.g., a pin) is removably attached to the distal end 13 of the light guiding tip 7. The fixation element 8 may be heated by the laser light until it becomes ductile. Each of the light guiding tips 7, 7', 7'', 7''' comprise fixation elements 8, 8', 8'', 8''' with different sizes. The light guiding tips 7, 7', 7', 7'' of FIGS. 2a to 2c comprise laser light absorbing means 6 to reduce a radiant flux $\Phi_1$ received from the hand piece 2 to a radiant flux $\Phi_2 < \Phi_1$ transmitted so that a total radiant energy $Q = \Phi_2 \cdot t_F$ is emitted from the laser source 3 and through the first optical waveguide 4 of the hand piece 2 and the second optical waveguide 12 of the light guiding tips 7 to the fixation element 8. The laser light absorbing means 6 thus permit the radiant flux $\Phi_2$ transmitted to the fixation element 8 to be set with a magnitude adjusted to the volume and/or surface of the fixation element 8. Additionally, when taken in combination with the fixed time period $t_F$ defined by the timer 10, the laser light absorbing means also automatically controls the total radiant energy $Q = \Phi_2 t_F$ so that no overheating or insufficient softening of the fixation element 8 occurs. FIG. 2d depicts a light guiding tip 7''' comprising no laser light absorbing means 6. In this embodiment, the unreduced radiant flux $\Phi_1$ of the laser source 3 is transmitted to the fixation element 8''' and the controlled total radiant energy results in $Q = \Phi_1 t_F$.

The laser light absorbing means 6 are provided in the form of elongated sticks 26 which can be attached to fibers of the optical waveguide 12. Specifically, a plurality of the elongated sticks 26 extend distally from the proximal end 11, each having a different length selected to conform to the requirements of a particular procedure. FIGS. 2a-2c depict various combinations of lengths of the elongated sticks 26 according to the invention. It is further noted, however, that any lengths and combinations of the sticks 26 may be employed without deviating from the scope of the invention. The elongated sticks 26 can consist of a metal with a high heat capacity (e.g., aluminum, iron, wax, paraffin or glass). In an alternate embodiment, the elongated sticks 26 can consist of plastic wax. In this embodiment, energy absorption of the light absorbing means 6 may be effected by changing the state of aggregation, e.g. when the plastic wax changes from a solid into a liquid. In another embodiment, the elongated sticks 26 may contain a colored fluid (e.g. water) housed therewithin. In this embodiment, energy transmitted from the laser source 3 through the internal optical waveguide 4 and the fibers of the optical waveguide 12 is absorbed by the colored fluid.

The fixation elements 8, 8', 8'', 8''' are provided in the form of pins and are clamped or otherwise attached to the distal end 13 of the light guiding tips 7, 7', 7'', 7''' and made available to an end-user in this form. When heated, the fixation elements 8, 8', 8'', 8''' may be easily detached from the light guiding tips 7, 7', 7'', 7'''. It is noted, however, that the fixation elements 8, 8', 8'', 8''' may be formed with any other shape and dimension without deviating from the scope of the invention.

FIG. 3 illustrates the hand piece 2 of FIG. 1 with the light guiding tip 7' of FIG. 2b attached thereto. The light guiding tip 7' is centered relative to the hand piece 2 by means of the cap 9. Due to the varying lengths of the elongated sticks 26 of FIG. 2b, a cross-sectional area of the optical waveguide 12 is reduced in a distal direction. It is therefore further noted that the light guiding tip 7' is particularly suitable for fixation elements 8' having different diameters, as those skilled in the art will understand.

Figure 4:
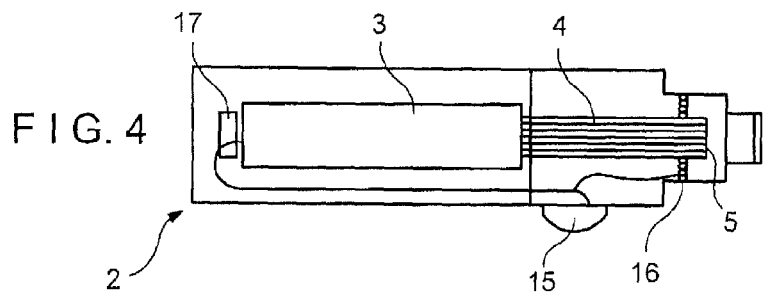
FIG. 4 illustrates a longitudinal section through the hand piece of a second kit according to the invention.
Figure 5A:
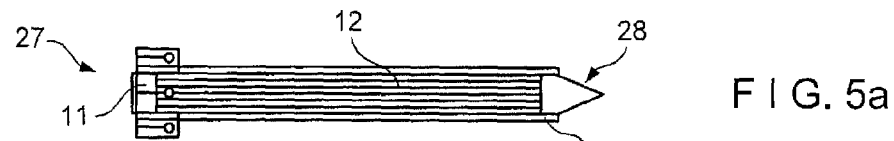
FIG. 5a illustrates a longitudinal section through a first light guiding tip for the second kit according to the invention.
Figure 5B:
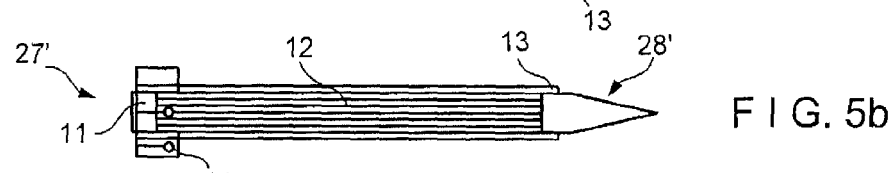
FIG. 5b illustrates a longitudinal section through a second light guiding tip for the second kit according to the invention.
Figure 5C:
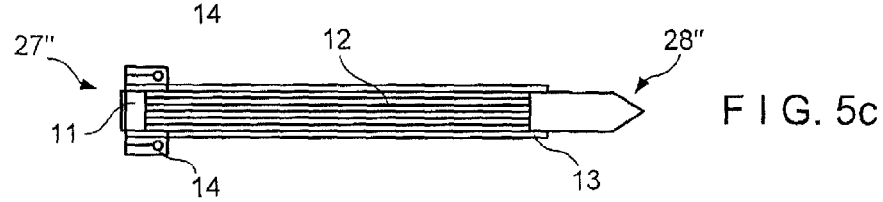
FIG. 5c illustrates a longitudinal section through a third light guiding tip for the second kit according to the invention.
Figure 5D:
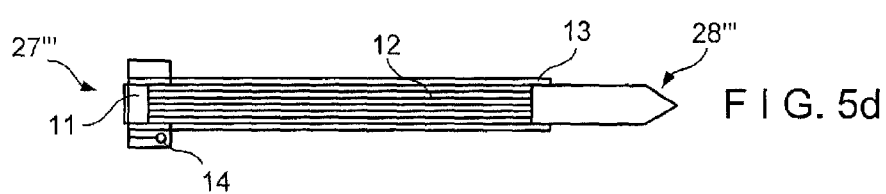
FIG. 5d illustrates a longitudinal section through a fourth light guiding tip for the second kit according to the invention.
Figure 6:
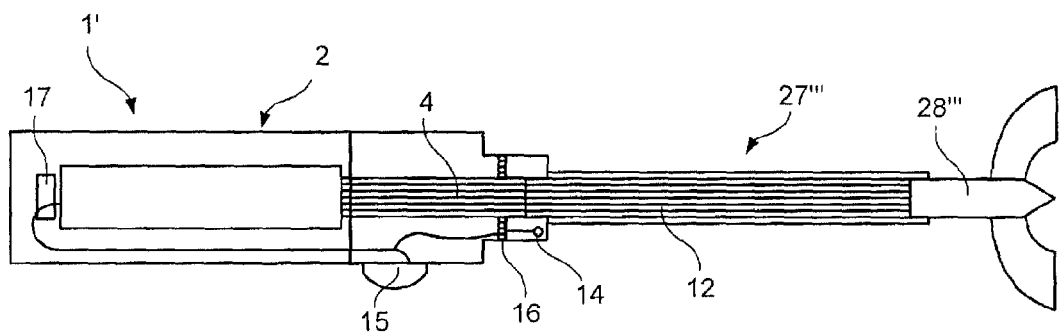
FIG. 6 illustrates a longitudinal section through the hand piece and a light guiding tip attached thereto of the second embodiment of the kit according to the invention.

FIGS. 4 to 6 depict a kit 1' according to a first alternate embodiment of the invention, the kit 1' being formed substantially similarly as the kit 1 of FIGS. 1-3, wherein like elements have been referenced with like reference numerals. The kit 1' comprises the hand piece 2 having the laser source 3 optically and mechanically connected to the internal optical waveguide 4. The internal optical waveguide 4 transports laser light emitted by the laser source 3 and a microprocessor 16 electronically connected to a timer 17. In the present embodiment, the laser source 3 is configured to emit a constant radiant flux $\Phi_1$. The internal optical waveguide 4 extends from the laser source 3 to the distal end 5 of the hand piece 2, which may be connected to the proximal end 11 of the light guiding tip 7. The trigger button 15 is provided on the hand piece 2 to actuate the timer 17 and activate the laser source 3.

The timer 17 is configured as an electronic chip and has a variable time $t_V$ defined and set by a set-point control 14 of the light guiding tip 7. Specifically, the set-point control 14 is configured to control the timer 17 to have a predetermined time period $t_V$ selected to apply a predetermined amount of laser light from the laser source 3, as will be described in greater detail later on. The microprocessor 16 is arranged on the hand piece 2 adjacent to the distal end 5 and comprises a number M of electrical contacts 21 so that the set-point control 14 of the light guiding tip 7 comprising the same number M of electrical contacts 21 may be electrically connected thereto.

FIGS. 5a-5d illustrate a selection of different light guiding tips 27, 27', 27'', 27''' according to the invention. Each light guiding tip 27, 27', 27'', 27''' extends from the proximal end 11 to the distal end 13. Fixation elements 28, 28', 28'', 28''' are removably attached to the distal ends 13, the fixation elements 28, 28', 28'', 28''' being configured to be heated by means of the laser light until they become ductile. Each of the light guiding tips 27, 27', 27'', 27''' is configured to receive a fixation element 28, 28', 28'', 28''' having a different diameter. Furthermore, each light guiding tip 27, 27', 27'', 27''' comprises the set-point control 14 electrically connectable to the microprocessor 16 of the hand piece 2 to determine the individual time period $t_V$ for the energy flow of the laser source 3 with respect to the fixation elements 28, 28', 28'', 28'''. The set-point control 14 is described in greater detail below with respect to FIGS. 13 to 16. Each light guiding tip 7 contains a different set-point control 14 that is configured with respect to the volume or surface of the individual fixation element 8.

FIG. 6 illustrates the hand piece 2 of FIG. 4 with the light guiding tip 27''' of FIG. 5d attached thereto. Due to the constant cross-sectional area of the optical waveguide 12 of the light guiding tip 27'', the embodiments of FIGS. 4 to 6 are particularly suitable for fixation elements 28, 28', 28'', 28''' that have the same diameter but different lengths.

In an operative configuration, the light guiding tip 27''' is connected to the hand piece 2 and actuation of the trigger button 15 permits the set-point control 14 to control the timer 17 to activate the laser source 3 for a time period $t_V$. A total radiant energy $Q=\Phi_1 t_V$ is then emitted from the laser source 3 through the internal optical waveguide 4 and the optical waveguide 12 to the fixation element 8. The individual time period $t_V$ defined by the set-point control 14 and the constant radiant flux L of the laser source 3 permit automatic control of the total radiant energy $Q=\Phi_1 t_V$ with respect to the fixation element 8 to prevent overheating or insufficient softening of the fixation element 8, as described in greater detail earlier.

Figure 7:
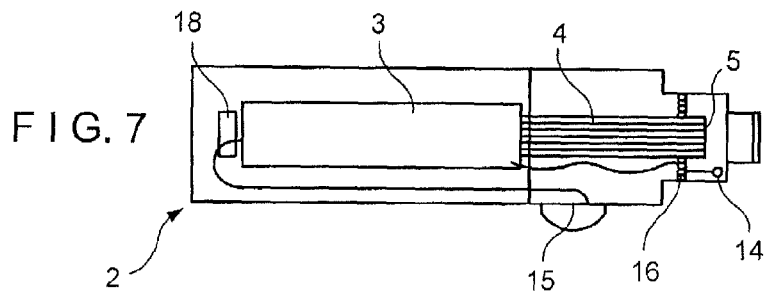
FIG. 7 illustrates a longitudinal section through the hand piece of a third kit according to the invention.
Figure 8A:
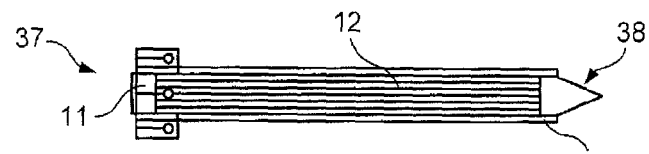
FIG. 8a illustrates a longitudinal section through a first light guiding tip for the third kit according to the invention.
Figure 8B:
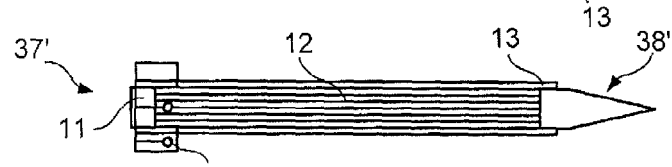
FIG. 8b illustrates a longitudinal section through a second light guiding tip for the third kit according to the invention.
Figure 8C:
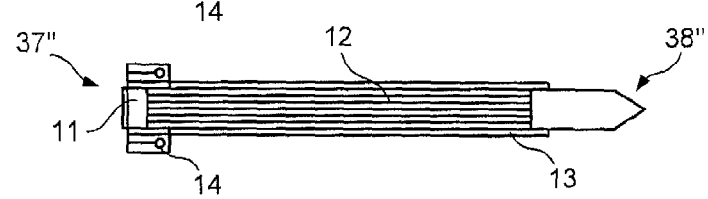
FIG. 8c illustrates a longitudinal section through a third light guiding tip for the third kit according to the invention.
Figure 8D:
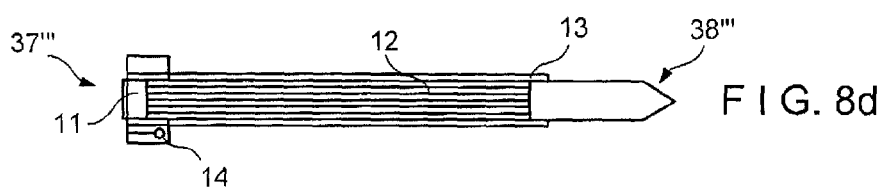
FIG. 8d illustrates a longitudinal section through a fourth light guiding tip for the third kit according to the invention.
Figure 9:
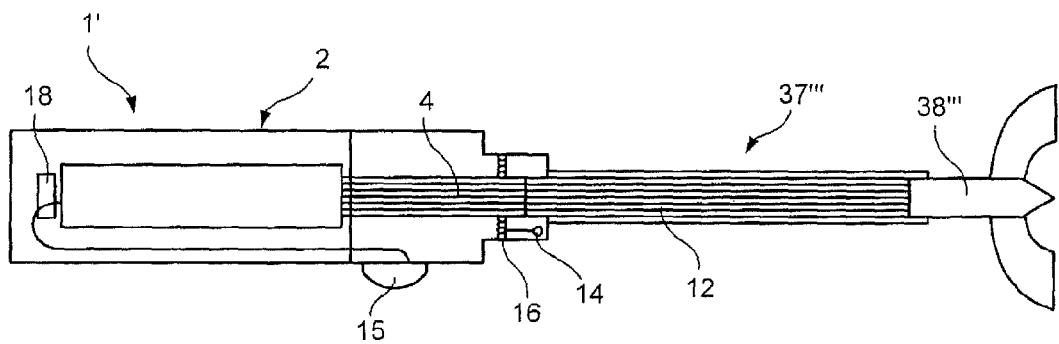
FIG. 9 illustrates a longitudinal section through the hand piece and a light guiding tip attached thereto of the third embodiment of the kit according to the invention.

FIGS. 7 to 9 depict a kit 1'' according to a third embodiment of the invention, the kit 1'' being formed substantially similarly as the kit 1 of FIGS. 1-4, wherein like elements have been referenced with like reference numerals. The kit 1'' comprises the hand piece 2 having the laser source 3 optically and mechanically connected to the internal optical waveguide 4. A timer 18 and a microprocessor 16 are electronically connected to the laser source 3. In the present embodiment the laser source 3 is configured to emit a variable radiant flux $\Phi_V$. The timer 18 is configured as an electronic chip and has a constant time period $t_F$. The microprocessor 16 controls the magnitude of radiant flux $\Phi_V$ as defined by the set-point control 14 of the light guiding tip 7 and which depends on the size of the fixation element 8.

FIGS. 8a to 8d illustrate a selection of different light guiding tips 37, 37', 37'', 37'''. Each light guiding tip 37, 37', 37'', 37''' extends from the proximal end 11 to the distal end 13 and is removably connectable to one of the fixation elements 38, 38', 38'', 38'''. Furthermore, each light guiding tip 37, 37', 37'', 37''' comprises the set-point control 14, which are electrically connectable to the microprocessor 16 of the hand piece 2 and determine the individual radiant flux $\Phi_V$ transmitted from the laser source 3 to the fixation element 8 via the microprocessor 16. Each light guiding tip 37, 37', 37'', 37''' contains a different set-point control 14 that is configured with respect to the volume or surface of the individual fixation element 38, 38', 38'', 38'''.

FIG. 9 illustrates the hand piece 2 of FIG. 7 and the light guiding tip 37''' of FIG. 8d attached thereto. Due to the constant cross-sectional area of the optical waveguide 12 of the light guiding tip 37''', the embodiment of FIG. 9 is particularly suitable for fixation elements 38''' that have the same diameter but different lengths.

Upon connection of the light guiding tip 37''' to the hand piece 2, the set-point control 14 induces the microprocessor 16 to control the magnitude of radiant flux $\Phi_V$. The timer 18 has a fixed time period $t_F$ to activate the laser source 3 so that after actuation of the trigger button 15, a total radiant energy $Q=\Phi_V t_F$ is emitted from the laser source 3 through the internal optical waveguide 4 and the optical waveguide 12 to the fixation element 8. By means of the constant time period $t_F$ defined by the timer 18 and the radiant flux $\Phi_V$ defined by the set-point control 14, the total radiant energy $Q=\Phi_1 t_V$ is automatically controlled so that no overheating or insufficient softening of the fixation element 38''' occurs.

Figure 10:
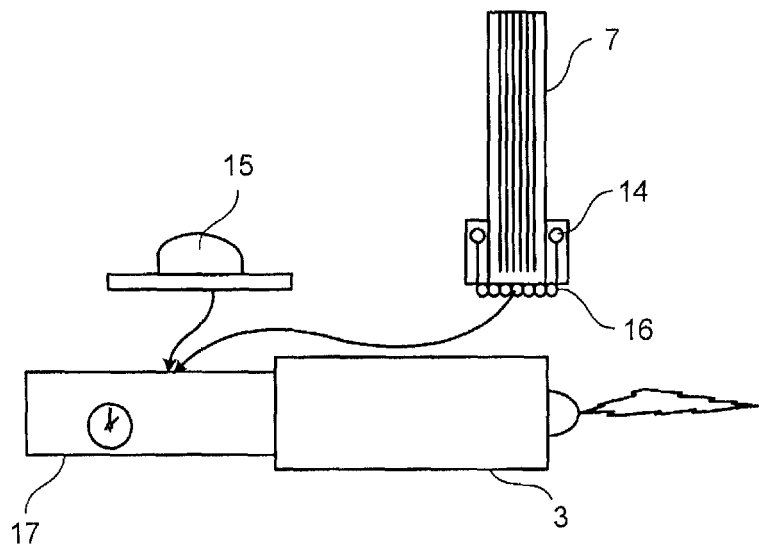
FIG. 10 illustrates a schematic view of the second embodiment of the kit according to the invention.

FIG. 10 illustrates an exemplary method of setting the time period $t_V$ of the timer 17 of the kit 1'. As described in greater detail hereinafter with reference to FIGS. 13-16, the set-point control 14 of the light guiding tip 7 provides a particular code to the microprocessor 16. The microprocessor 16 then reports a period to the timer 17 on the basis of the code. Actuation of the trigger button 15 then causes the timer 17 to run.

Figure 11:
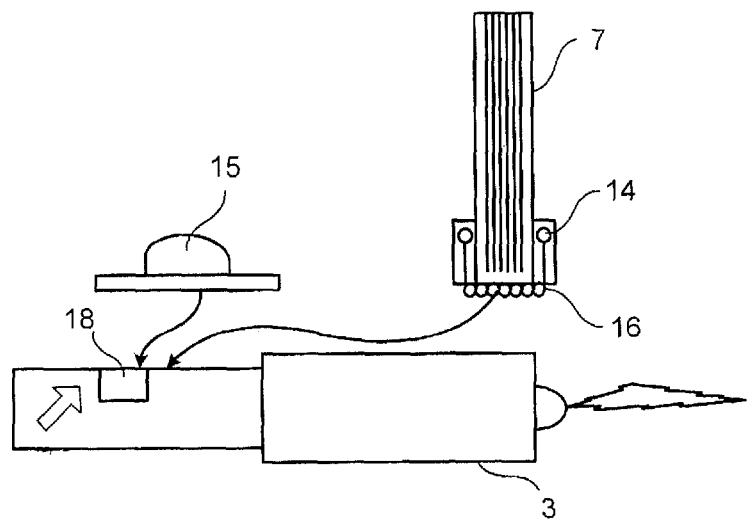
FIG. 11 illustrates a schematic view of the third embodiment of the kit according to the invention.

FIG. 11 illustrates an exemplary method of operation of the kit 1''. Specifically, FIG. 11 illustrates how the power of the source of laser 3 of the kit 1'' is set. The light guiding tip 7 provides a code to the microprocessor 16 on the basis of the set-point control 14. The microprocessor 16 then reports the power in Watts of the laser source 3 on the basis of the known code. Upon actuating the trigger button 15, the laser source 3 produces energy with power supplied thereto. A simultaneous activation of the constant timer 18 switches off the laser source 3 after the fixed period of time has elapsed.

FIG. 12 illustrates a variant of the laser light absorbing means 6 used in the kit 1 of FIGS. 1 to 3. In this embodiment, the laser light absorbing means 6' is configured as energy absorbing glass capsule 19 which absorbs the laser light of the laser source 3. A colored fluid 20 (e.g., water) is encased within the glass capsule 19 to absorb the laser light and evaporate. In an exemplary embodiment, the capsule 19 may be embedded within a disposable tip (not shown) configured for removable attachment to the distal end of the hand piece 2, the disposable tip being further configured for removable attachment to a bone fixation element, as described in greater detail with respect to earlier embodiments.

FIGS. 13 to 15 illustrate the microprocessor 16 electrically connected to the set-point control 14', 14'', 14''' via a number M=3 of electrical contacts 21 and the grounding 22. The set-point control 14', 14'', 14''' comprise a code block 23 with a number P≤M of code pins 24. Each code pin 24 activates one electrical contact 21 by electrically connecting the electrical contact 21 to the grounding 22, as those skilled in the art will understand. The number P and position of the activated code pins 24 defines a particular code, which is turn used to determine the time period $t_V$ or the magnitude of radiant flux $\Phi_V$ to the microprocessor 16.

The table shown in FIG. 16 illustrates the definition of different codes 0 to 7 wherein an inactive electrical contact 21 is by "0" and an activated electrical contact 21 is "1". For example, Code 0 defines that a number P=0 of electrical contacts 21 is activated. Codes 1 to 3 define that a number P=1 of electrical contacts 21 is activated and the position of the activated electrical contacts 21. Codes 4 to 6 define that a number P=2 of electrical contacts 21 is activated and the position of the activated electrical contacts 21. Code 7 defines that a number P=3 of electrical contacts 21 are activated.

The set-point control 14' illustrated in FIG. 13 defines Code 0 where a number P=0 of electrical contacts 21 is activated. The code block 23 comprises no code pins 24 so that none of electrical contacts 21 is connected to the grounding 22. The set-point control 14'' illustrated in FIG. 14 defines Code 1 where the first one of the three electrical contacts 21 is activated. The set point control 14''' of FIG. 15 illustrates Code 7 where all three electrical contacts 21 are activated.

Although the invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

It will be appreciated by those skilled in the art that various modifications and alterations of the invention can be made without departing from the broad scope of the appended claims. Some of these have been discussed above and others will be apparent to those skilled in the art.

What is claimed is:

1. A device for implanting at least one bone fixation element in a bone, comprising:
    a bone fixation element comprising thermoplastic material and defining a proximal surface area at a proximal portion thereof;
    a hand piece that defines a proximal end and a distal end opposite the proximal end, the hand piece including a laser source configured to emit a radiant flux $\phi_1$ and the hand piece further including a first internal optical waveguide connected to the laser source and open at the distal end of the hand piece; and
    a light guiding tip having a proximal end and a distal end opposite the proximal end, the light guiding tip including a second optical waveguide, the proximal end of the light guiding tip being configured to mechanically, optically and removably connect to the distal end of the hand piece, and the distal end of the light guiding tip being configured to permit removable attachment of the bone fixation element thereonto,
    and a controller configured to recognize the light guiding tip connected to the hand piece and in response to automatically adjust a total radiant energy Q transmitted from the laser source to the bone fixation element based on the light guiding tip connected to the hand piece and the proximal surface area of the bone fixation element.

2. The device of claim 1, further comprising a timer configured to control operation of the laser source.

3. The device of claim 1, wherein the bone fixation element is a bone pin.

4. The device of claim 1, further comprising a laser source provided in the hand piece.

5. The device of claim 1, wherein the first internal optical waveguide comprises a colored substance.

6. The device of claim 1, wherein the controller is configured to automatically adjust the total radiant energy by adjusting a timer to control the duration of the radiant flux emitted by the laser source, wherein the radiant flux is constant.

7. The device of claim 1, wherein the controller is configured to automatically adjust the total radiant energy by adjusting the radiant flux emitted by the laser source and using a timer to keep a duration of the radiant flux constant.

8. The device of claim 1, wherein the total radiant energy Q is transmitted from the laser source through the first optical wave guide of the hand piece and through the second optical wave guide of the light guiding tip to the bone fixation element.

9. The device of claim 1, wherein the light guiding tip further comprises a laser light absorbing means that is configured to reduce the radiant flux $\Phi_1$ emitted from the laser source to a radiant flux $\Phi_2$.

10. The device of claim 9, wherein the laser light absorbing means comprise elongated sticks.

11. The device of claim 10, wherein the elongated sticks comprise one of a metal or a plastic wax.

12. The device of claim 10, wherein the elongated sticks contain a colored substance housed therein.

13. The device of claim 9, wherein the magnitude of the total radiant energy Q transmitted from the laser source to the bone fixation element is further adjusted by the laser light absorbing means.

14. The device of claim 1, wherein the fixation element is softened upon application of the radiant energy Q to the proximal portion thereof.

* * * * *